United States Patent [19]
Homuth et al.

[11] Patent Number: 5,836,302
[45] Date of Patent: Nov. 17, 1998

[54] BREATH MONITOR WITH AUDIBLE SIGNAL CORRELATED TO INCREMENTAL PRESSURE CHANGE

[75] Inventors: James R. Homuth, DeForest; Kevin G. Tissot, Brooklyn, both of Wis.

[73] Assignee: Ohmeda Inc., Liberty Corner, N.J.

[21] Appl. No.: 889,911

[22] Filed: Jul. 10, 1997

Related U.S. Application Data

[60] Provisional application No. 60/027,933 Oct. 10, 1996.

[51] Int. Cl.⁶ .............................. A62B 9/00; A62B 7/00; G10K 9/00; G01L 7/00
[52] U.S. Cl. ............................... 128/205.23; 128/202.22; 128/204.21; 128/204.22; 600/529; 600/532; 116/266; 116/142 FP; 73/1.59; 73/1.71; 73/31.04; 73/700
[58] Field of Search ........................ 128/202.22, 204.18, 128/204.21–204.23, 205.23; 600/529, 532; 116/201, 200, 266, 268, 137 R, 140, 142 FP, DIG. 7, DIG. 18, DIG. 19; 73/1.57, 1.59, 1.71, 31.04, 712, 700

[56] References Cited

U.S. PATENT DOCUMENTS

| | | | |
|---|---|---|---|
| 2,376,971 | 5/1945 | Kleit | 128/207.13 |
| 2,904,033 | 9/1959 | Shane | 128/205.23 |
| 3,565,058 | 2/1971 | Mansfield . | |
| 3,611,178 | 10/1971 | McConnell | 128/202.22 |
| 3,648,686 | 3/1972 | Payne . | |
| 3,689,832 | 9/1972 | Leto et al. . | |
| 3,760,100 | 9/1973 | Ragsdale et al. . | |
| 3,830,227 | 8/1974 | Green . | |
| 3,867,934 | 2/1975 | Ollivier | 128/202.22 |
| 4,063,550 | 12/1977 | Tiep . | |
| 4,074,710 | 2/1978 | Tiep . | |
| 4,383,534 | 5/1983 | Peters | 128/207.15 |
| 4,576,178 | 3/1986 | Johnson . | |
| 4,602,644 | 7/1986 | DiBenedetto et al. | 128/207.18 |
| 5,095,896 | 3/1992 | Omoigul . | |
| 5,095,900 | 3/1992 | Fertig et al. . | |

*Primary Examiner*—Kimberly L. Asher
*Attorney, Agent, or Firm*—Roger M. Rathbun

[57] ABSTRACT

An audible waveform system is provided that senses a parameter relating to the ventilation of a patient. The system produces short bursts of sound of a predetermined frequency as the changes occur in that parameter based on certain increments of change. The bursts themselves are preferable at a frequency that is the same for equal pressures but increases and decreases in frequency as the parameter increases or decreases, respectively. In the preferred embodiment, the system provides an audible waveform based on the pressure in the patient airway so that the clinician can receive information relating to that waveform conveniently and without taking attention away from other monitors and/or alarms.

13 Claims, 3 Drawing Sheets

BREATH MONITOR WITH AUDIBLE SIGNAL CORRELATED TO INCREMENTAL PRESSURE CHANGE

This application is based upon Provisional Patent Application 60/027,933 filed Oct. 10, 1996.

BACKGROUND

This invention relates to the use of audio sounds to indicate a monitored parameter, and, more particularly, to a preferred use audio system where an audio sound conveys information relating to a waveform, preferably a pressure waveform representative of the pressure within the airway of a patient undergoing ventilation in a hospital environment.

In the normal operating room, there are various visual alarms and audible devices that are used to indicate certain parameters relating to the ventilation of a patient, whether good or bad. The clinician is required to monitor the various gauges, screens, dials etc. on the anesthesia machine and the ventilator to continually assure that the patient is receiving the proper care during an operation. It is, therefore, sometimes difficult for the clinician to monitor all of the required visual devices that are in the surroundings and which need constant review and assimilation of the information. At times the differing visual monitors, audible alarms and the like can become distracting to the clinician.

One parameter that is almost always monitored in administering breaths to the patient is the pressure in the patient airway and that pressure follows a certain waveform that would indicate that the patient is receiving a breath and exhaling under the desired conditions. While the monitoring of that pressure is an easy task for the ventilator, the difficulty is in communicating that information to the clinician in an easy, convenient manner and which does not take too much of the clinician's attention and thus divert that attention from other important matters at hand.

Accordingly it would be advantageous for the clinician to have some means of monitoring the airway pressure without taking the clinician's attention away from the other tasks or having to continually observe a pressure gauge or other visual device to obtain current and accurate information.

SUMMARY OF THE INVENTION

The present invention is particularly adapted to be used in monitoring one or more parameters relating to a patient undergoing ventilation and which may be interpreted by the clinician as indicating a certain ventilation to the patient without requiring a visual monitor. The present invention provides an audible indication of a monitored parameter and specifically, the pressure of the gas in the patient's airway during ventilation. Accordingly, the clinician can pay more attention to the other patient conditions indicated on the ventilator or anesthesia machine and yet can listen to the audible tones from the present invention and continually monitor the overall ventilation of the patient. One of the advantages is that the sounds are not continual and only are activated in changing conditions, thus if there is no actual change in the parameter, the audible sound is not active and the clinician does not have an additional sound to hear and interpret. Absence of sound may also indicate an important clinical condition when the value of the parameter is expected to change on a regular basis, as is the case with airway pressure during mechanical ventilation of a patient.

The present invention provides a sound of a short duration in the form of a burst when the particular parameter being monitored changes by a predetermined incremental amount, that is, as the pressure in the patient circuit rises, a sound occurs of a short duration based on a certain increment of pressure rise. Preferable, each increment of pressure has its own identifiable frequency and quality so that the clinician can merely listen to the audio output and be assured that the ventilator is providing a breath to the patient of the correct pressure and that a proper waveform of that pressure is being administered.

In a patient ventilation cycle, the ventilator provides a breath to the patient and thus the pressure in the patient airway increases during an inhalation cycle and then decreases as the ventilator enters the exhalation cycle and the patient exhales. In the preferred embodiment, the short bursts of sound increase in frequency at each incremental increase in pressure during the inhalation cycle and then decrease in the same manner during exhalation as the airway pressure decreases. The bursts of sound may be emitted, for example, every 2 cm.$H_2O$ as the pressure changes during inhalation and exhalation and by listening, the clinician will know that a proper inhalation and exhalation has been achieved without being distracted or taking attention away from the visible monitors or carrying out the visual monitoring of the patient.

It the more preferred embodiment, the frequency of the audible bursts are proportional to the airway pressure so that a particular audible burst will be at the same frequency at the same pressure, that is, the clinician will hear the same sound at a particular specific airway pressure whether in the inhalation cycle or the exhalation cycle. Thus, the sounds will increase in frequency as the patient airway pressure increases and will decrease in frequency as the patient airway pressure decreases, yet at any particular pressure, the burst of audible sound will be at the same frequency.

As a further feature, in transformation from a patient to relying totally upon a ventilator to spontaneous breathing, any attempt to inhale by the patient is significant and with the present audible waveform, the drawing of a breath by the patient creates a slight negative pressure in the airway. With the present invention, a smaller incremental change may be detected to be able to sense that small negative pressure and, due to the flexibility of assigning a variety of sounds to the reaching of any incremental change in pressure, the sound assigned may be of a higher volume and an appropriate frequency to indicate to the clinician the fact that the patient is trying to breath spontaneously. The sound itself may be chosen, for example, as a clarinet at low frequencies and at higher volume so that such important information can easily be heard and interpreted by the clinician.

DETAILED DESCRIPTION OF THE INVENTION

Figure 1:
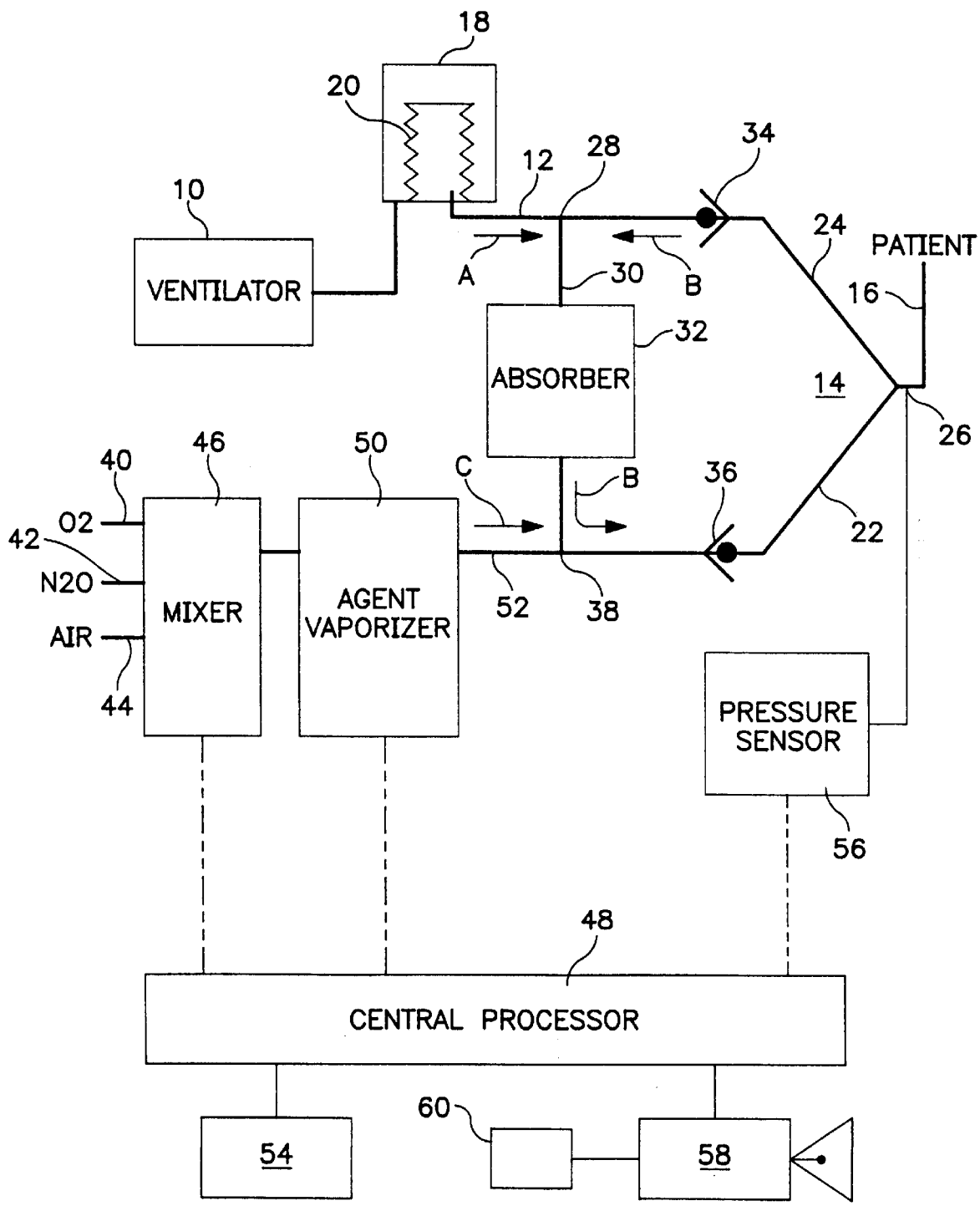
FIG. 1 is a block diagram of an anesthesia system incorporating the audible waveform system of the present invention.

Referring now to FIG. 1, there is shown a block diagram of an anesthesia system including the audible waveform system of the present invention. As will be seen, the audible waveform is preferably used in a ventilation system for a patient in a hospital environment and will be described as such for the preferred embodiment, however, it will be understood that the audible waveform of the present invention described herein can be used for considerable other purposes and with other systems.

As shown, a ventilator 10 is provided and which may be of the type shown and described in U.S. Pat. No. 5,315,989 assigned to the present applicant and the disclosure of which is incorporated herein by reference. That ventilator 10 of the aforementioned U.S. Patent has an inhalation cycle and an exhalation cycle controlled by a CPU.

The ventilator 10 provides gas to the patient during the inhalation cycle via a conduit 12 to the patient breathing circuit 14 where it is delivered to the patient 16. The ventilator 10 typically includes a bellows assembly 18 and air or other powering gas is supplied to the bellows assembly 18 exterior of the bellows 20 by the ventilator 10 via a conduit 11 and which then collapses the bellows 20 to force gases within the bellows 20 to the patient 16.

As also noted in the aforementioned U.S. Patent, the patient breathing circuit 14 itself conventionally includes an inspiratory limb 22 and an expiratory limb 24 and the patient is connected to a wye connection 26 located intermediate the inspiratory and the expiratory limbs 22, 24. The means of connection may be an endotracheal tube, face mask or other interface between the patient 16 and the patient breathing circuit 14.

In conventional operation, gas is delivered to the patient 16 by means of a powering gas that collapses the bellows 20 to drive the gas into conduit 12 and then into the tee 28 where the gas enters a conduit 30 and passes through an absorber 32. After passing through the absorber 32, the gas enters the inspiratory limb 22 of the patient breathing circuit 14 to be administered to the patient 16. As the patient exhales, that exhalation, now laden with $CO_2$, passes through the expiratory limb 24 where it again passes through the tee 28 and continues to the absorber 32 where the $CO_2$ is eliminated by a $CO_2$ absorbing material, such as soda lime.

A pair of check valves 34 and 36 are positioned in the patient breathing circuit 14 in the expiratory and inspiratory limbs 24 and 22, respectively, to maintain the flow of gas in the proper direction around the circle patient breathing circuit 14.

A flow of fresh gas is also introduced into the patient breathing circuit 14 and, as shown, is added at a tee 38 and thus into the inspiratory limb 22 of the patient breathing circuit 14. That flow of fresh gas is provided from a source of gas, typically oxygen and air, and may include nitrous oxide to aid in anesthetizing the patient. As shown in FIG. 1, there is a supply of oxygen 40, nitrous oxide 42 and air 44 and such supply may be through a central piping system of a hospital or may be through the use of individual cylinders of such gases.

In any event, the gases are mixed in a gas mixer 46 in the proportion desired by the user. The actual control of the proportions and the flow through the gas mixer 46 is, in the preferred embodiment, controlled by a central processing unit (CPU) 48. The mixed gases from the gas mixer 46 then pass through an agent vaporizer 50 where liquid anesthetic agent is vaporized and added to the stream of gas such that anesthetic laden gas continues into a conduit 52 and enters the patient breathing circuit 14 at the tee 38.

The CPU 48 controls the agent vaporizer 50 and which determines the percentage concentration of anesthetic agent that is in the gas that enters the patient breathing circuit 14 and thus that is supplied to the patient to induce and maintain anesthesia.

The CPU 48 is, in turn, controlled by an input device 54 provided so that the clinician can input the data needed to determine the various parameters to provide the flow and anesthetic concentration desired to anesthetize the patient.

In the overall flow scheme of the present conventional system, the gas is forced by the ventilator 10 into conduit 12 in accordance with the arrow A during the inhalation cycle of the patient 16. That air thus passes through the tee 28 and through absorber 32 where it further passes through tee 38 and into the inspiratory limb 22 of the patient breathing circuit 14. At that tee 38, fresh gas containing a predetermined concentration of an anesthetic agent is joined with the gases from the ventilator and proceeds with the gases already circulating in patient breathing circuit 14 and administered to the patient 16.

When the patient exhales, the exhaled gases pass through the expiratory limb 24 of the patient breathing circuit 14 through tee 28 and continue through the circuit, passing though the absorber 32 where the gases are scrubbed to eliminate the $CO_2$ that is exhaled by the patient 16.

As can be seen, therefore, the anesthesia system is basically a circle system where the gases continue to pass in a circle as shown by the arrows B with the addition of fresh gas and the anesthetic agent added to those gases in the direction of Arrow C as the gases pass around the circle portion of the circle system.

As a further component of the overall anesthesia system, a pressure monitor 56 is provided to detect the pressure of the gas in the patient breathing circuit 14. That pressure is monitored continuously and is normally displayed on the anesthesia machine by means of a visual display such as a pressure gauge.

The signals from pressure monitor 56 representative of the monitored pressure within the patient breathing circuit 14 are transmitted to CPU 48 where they are further processed in carrying out the present invention. In particular, as will be seen, eventually signals are sent by CPU 48 to an audio output device 58 where certain sounds are generated or, alternatively, the sounds are retained in a memory 60 and provided to audio output device 58 so that certain well recognized sounds can be used.

Figure 2:
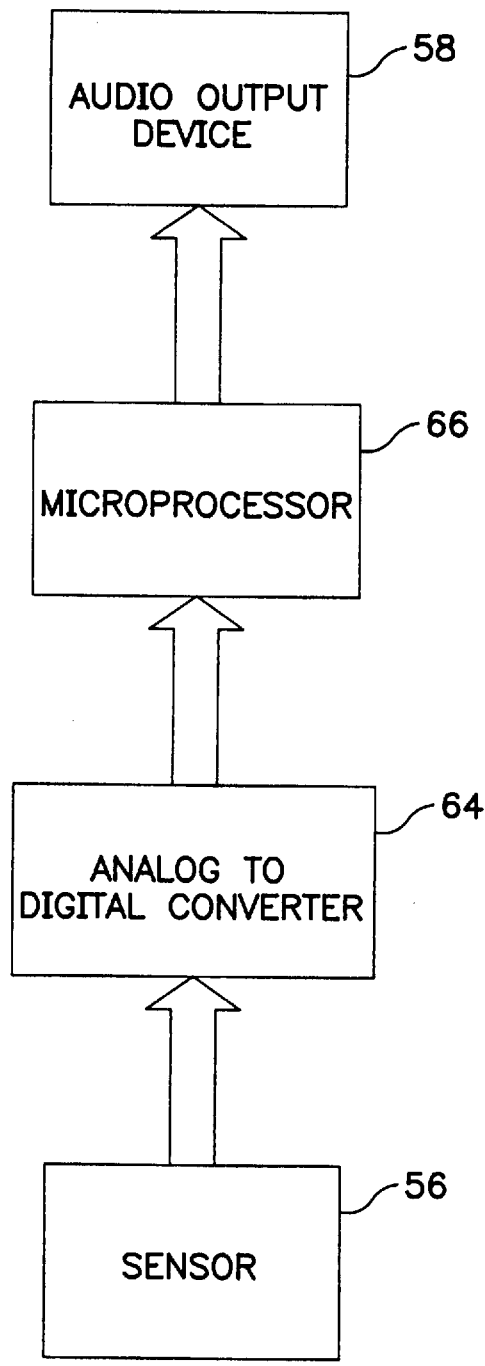
FIG. 2 is a block diagram of the components of the present invention.

Turning now to FIG. 2, there is shown a block diagram of the audio waveform system of the present invention. As shown the signals fro the pressure transducer 56 representative of the particular parameter being monitored, in the preferred embodiment, the pressure within the patient breathing circuit 14 are sent to an analog to digital converter 64 where the signals are digitized. Those digital signals are then sent to a microprocessor 66 where the signals are analyzed and a further signal generated each time the digitized signals indicate that the pressure within the patient breathing circuit 14 has changed by a predetermined increment, such as every 2 cm.$H_2O$ in either direction, i.e. increase or decrease in pressure.

That signal is thus transmitted to the audio output device 58 where a burst of sound of a particular frequency is emitted to be heard by the clinician. The burst of sound may be generated by a tone generator embodied in the audio output device 58 or, alternatively, the particular sounds may be stored in a memory 60 (FIG. 1) where any particular representative frequency or sound quality may be used. As an example, the sounds of a particular musical instrument, such as a flute, may be stored at differing frequencies in the memory 60 and as each pressure increment change occurs, the sound of a flute may emanate from the audio output device 58 of the particular frequency for that particular pressure.

Figure 3:
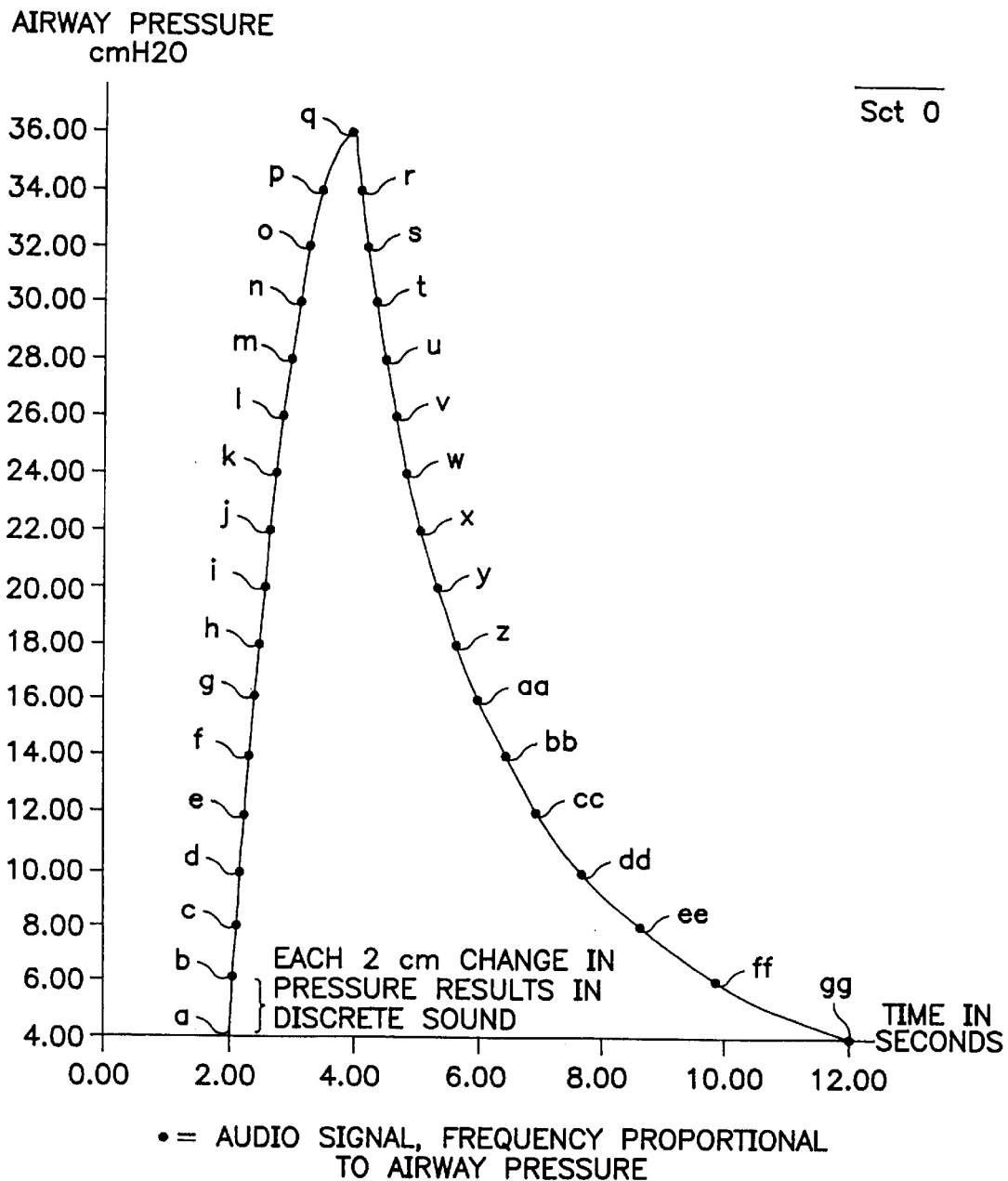
FIG. 3 is a typical waveform of the pressure in a patient airway during a breath administered to a patient by a ventilator.

Turning now to FIG. 3, there is shown a typical representative waveform of the pressure in the patient circuit during a full breath cycle delivered by a ventilator. As can be seen, the pressure rises as the breath is delivered and certain increments of pressure are reached, indicated generally by the points a through q. After pressure reaches a maximum at [point q, the pressure declines during the exhalation cycle and again, the points are indicated as r through gg. In carrying out the preferred embodiment of the present invention, at each of the points indicated by a letter, a short burst of sound is emitted by the audio output device 58 and more preferable, the frequency of the sounds increases as the pressure increases, thus, the frequency is proportional to the pressure and follows the waveform of the pressure in the patient circuit. At each specific pressure the particular frequency is preferably the same, that is, at, for example, the point g where the pressure in the patient breathing circuit is 20 cm.$H_2O$, a particular frequency burst of sound is emitted. At point aa, as the pressure is being reduced, at that same pressure, 20 cm.$H_2O$, the same frequency is preferably used. Thus, as the pressure increases and decreases, the clinician will hear the same overall range of frequencies and will be able to note that the pressure has risen, fallen and generally returned to the starting point by listening to the frequencies of the bursts of sound.

As indicated, by use of the present invention, the sound itself may be chosen from any variety of sounds contained in memory and the sounds may differ by instrument voice, as between a flute or a clarinet, timbre, amplitude, frequency and stepwise per burst, that is, the incremental change that must be reached to activate the burst of sound.

In particular, it is important during mechanical ventilation to be able to detect the patient attempting to breathe spontaneously. With the present invention, therefore, the change in pressure as a slight negative pressure is drawn by the patient within the airway, can thus be assigned a unique sound that may be more readily picked up by the clinician and the incremental change that causes that burst of sound to be a smaller increment than in sensing the positive pressure portions of the waveform. Thus, when sensing the negative pressure indicative of the patient attempting to breath spontaneously the invention may use low frequencies sounds of a clarinet and the volume increased. In that way, the clinician can readily distinguish the sounds of the patient attempting to breath and take the appropriate action. Thus, it is advantageous in the present invention to be able to select the particular incremental change that must be reached to activate the burst of sound as well as to select any one or more of a variety of sounds retained in the memory, including the instrument voice, timbre, amplitude, frequency and incremental step sensed to activate the burst of sound.

Numerous further variations and combinations of the features discussed above can be utilized without departing from the spirit of the invention as defined by the claims below. Accordingly, the foregoing description of the preferred embodiment should be taken by way of illustration rather than by way of limitation of the invention as claimed.

We claim:

1. An anesthesia system for providing a breath cycle to a patient of varying pressure and having a sound output indicative of a parameter of the breath, said anesthesia system comprising:
   a patient circuit, a ventilator providing a breath to a patient at varying pressure following ;3 waveform through a said patient circuit,
   a sensor to continuously monitor the varying pressure within said patient circuit,
   processor means to determine a predetermined incremental change in pressure monitored by said sensor and to provide a signal when said predetermined incremental change has been determined, and
   an audible output device responsive to said signal from said processor to produce a burst of sound of a predetermined frequency.

2. An anesthesia system for providing a breath cycle to a patient of varying pressure as defined in claim 1 wherein said predetermined frequency is based upon the pressure sensed by said sensor in said patient circuit.

3. An anesthesia system for providing a breath cycle to a patient of varying pressure as defined in claim 2 wherein said predetermined frequency is proportional to the pressure sensed by said sensor in said patient circuit.

4. An anesthesia system for providing a breath cycle to a patient of varying pressure as defined in claim 3 wherein said predetermined frequency is the same for the same pressure value in said patient circuit.

5. An anesthesia system for providing a breath cycle to a patient of varying pressure as defined in claim 4 wherein said audible output device includes a plurality of sounds retained in memory and audible output device selects a particular sound from said memory depending upon the pressure in said patient circuit.

6. An anesthesia system for providing a breath cycle to a patient of varying pressure as defined in claim 1 wherein said predetermined frequency is based upon a negative pressure sensed by said sensor in said patient circuit.

7. A method of providing an audible waveform in a ventilator system providing a breath cycle to a patient of varying pressure comprising the steps of:
   (a) providing a breath of varying pressure to a patient;
   (b) sensing and monitoring the pressure of the breath provided to a patient,
   (c) determining predetermined incremental changes in the pressure of the breath sensed and monitored in step (b),
   (d) providing an audible sound of predetermined frequency at each predetermined incremental change in pressure determined in step (c).

8. A method of providing an audible waveform in a ventilator system as defined in claim 7 wherein said step of providing an audible sound of predetermined frequency includes determining said predetermined frequency based on the pressure sensed in step (b).

9. A method of providing an audible waveform in a ventilator system as defined in claim 7 wherein said step of providing an audible sound of predetermined frequency includes determining said predetermined frequency so as to be proportional to the pressure sensed in step (b).

10. A method of providing an audible waveform in a ventilator system as defined in claim 7 wherein said step of sensing and monitoring the pressure of the breath provided to a patient comprises sensing a negative pressure.

11. A method of providing an audible waveform in a ventilator system as defined in claim 7 wherein said step of sensing and monitoring the pressure of the breath provided to a patient comprises sensing a negative pressure and a positive pressure and said predetermined incremental steps are determined to be different incremental steps for negative pressures than for positive pressures.

12. A method of providing an audible waveform in a ventilator system as defined in claim 11 wherein said predetermined incremental steps are determined to be smaller incremental steps for negative pressures than for positive pressures.

13. A method of providing an audible waveform in a ventilator system as defined in claim 11 wherein said sounds provided for said positive and said negative pressures differ in quality by a property selected from the group comprising instrument voice, timbre and amplitude.

* * * * *